US008895472B2

(12) United States Patent
Yang et al.

(10) Patent No.: US 8,895,472 B2
(45) Date of Patent: Nov. 25, 2014

(54) AGENT FOR REDUCING NICOTINE AND HARMFUL COMPONENTS IN TOBACCO LEAVES FOR USE IN FIELD CULTIVATION OF TOBACCO

(75) Inventors: Chunlei Yang, Hubei (CN); Shu Yang, Hubei (CN); Jinpeng Yang, Hubei (CN); Kaixiao Fan, Hubei (CN); Wenzhang Qin, Hubei (CN); Candong Deng, Hubei (CN)

(73) Assignee: Tobacco Research Institute of Hubei Province, Wuhan, Hubei (CN)

( * ) Notice: Subject to any disclaimer, the term of this patent is extended or adjusted under 35 U.S.C. 154(b) by 130 days.

(21) Appl. No.: 13/319,902

(22) PCT Filed: May 11, 2010

(86) PCT No.: PCT/CN2010/072628
§ 371 (c)(1),
(2), (4) Date: Nov. 10, 2011

(87) PCT Pub. No.: WO2010/130197
PCT Pub. Date: Nov. 18, 2010

(65) Prior Publication Data
US 2012/0065069 A1    Mar. 15, 2012

(30) Foreign Application Priority Data
May 12, 2009    (CN) .......................... 2009 1 0062059

(51) Int. Cl.
A01N 43/36    (2006.01)
A01N 37/40    (2006.01)
A01G 7/06    (2006.01)
A01H 3/04    (2006.01)
A01N 37/10    (2006.01)

(52) U.S. Cl.
CPC ........ *A01N 37/40* (2013.01); *A01G 7/06* (2013.01); *A01H 3/04* (2013.01); *A01N 37/10* (2013.01)
USPC ........................................................ 504/138

(58) Field of Classification Search
None
See application file for complete search history.

(56) References Cited

U.S. PATENT DOCUMENTS

| 7,691,630 B2 | 4/2010 | Moon et al. | |
| 2005/0072047 A1* | 4/2005 | Conkling et al. | 47/58.1 FV |

FOREIGN PATENT DOCUMENTS

| CN | 1351852 A | 6/2002 |
| CN | 1476756 A | 2/2004 |
| CN | 1579260 A | 2/2005 |
| CN | 1580237 A | 2/2005 |
| CN | 1654632 A | 8/2005 |
| CN | 1654633 A | 8/2005 |
| CN | 1757337 A | 4/2006 |
| CN | 101015391 A | 8/2007 |
| CN | 101070535 A | 11/2007 |
| CN | 101288504 A | 10/2008 |
| CN | 101548673 A | 10/2009 |

OTHER PUBLICATIONS

State Intellectual Property Office of the People's Republic of China, "Office Action", China, Nov. 24, 2011.
State Intellectual Property Office of the People's Republic of China, "Notice of Allowance", China, May 4, 2012.
Ding Feng, Regulating Effect of Nicotine Content of Flue-Cured Tobacco with Exogenous Regulators, Thesis for Degree of Master, Nanjing Agricultural University, Sep. 2006, p. 1-65.
Liu, Huashan et al., Effects of exogenous IAA on activity of ODC, MPO, MPT and nicotine content in flue-cured tobacco, Acta Tabacaria Sinica, 2005, p. 41-43, vol. 11, No. 6.
Gao, Wenxia et al., Effects of Nitrogen, Remained Leaves and a-NAA on the Nicotine of Flue-Cured Tobacco Variety K326, Journal of Shanxi Agricultural University, 2005, p. 207-210, vol. 25, No. 3.
Xin Sun et al., Effects of Salicylic Acid on Several Physiological Indexes of Kidney Bean under Water Stress, Journal of Sichuan University, 2005, p. 575-579, vol. 42, No. 3.
Yifan Zhang et al., Discussion on Physiological Effect of Salicylic Acid in Plants, China new Technologies and Products, 2009, vol. 1.
Kang, Guozhang et al., Effect of Salicylic Acid on Respiration of Chilling-stressed Banana Seedlings, Guihaia, Jul., 2004, p. 359-362, vol. 24, No. 4.
Jian, Yongxing et al., Effect of Binding the Stem Tops after Topping with Tampons Soaked with a-NAA Solution on Nicotine Content and Sugar-nicotine Ratio in the Upper Leaf of Flue-cured Tobacco, Crops, Dec. 2008, p. 8-13.
Han, Jinfeng et al., Effect of Application of Plant Regulators on Nicotine Concentration in Tobacco, Acta Tabacaria Sinica, Jun. 2001, p. 22-25, vol. 7, No. 2.

* cited by examiner

*Primary Examiner* — Snigdha Maewall
(74) *Attorney, Agent, or Firm* — Tim Tingkang Xia, Esq.; Morris, Manning & Martin, LLP

(57) ABSTRACT

One aspect of the invention provides an agent for reducing nicotine and harmful components in tobacco leaves for use in the field cultivation of tobacco. In one embodiment, the agent contains (in a weight percentage): salicylic acid 0.005-0.16%, naphthaleneacetic acid 0-0.003%, indoleacetic acid 0-0.015%, and clean water added to 100%. The composition can significantly reduce nicotine and harmful components in tobacco leaves by applying it to tobacco plant in top pruning period of tobacco. The combination of salicylic acid, naphthaleneacetic acid and indoleacetic acid provides synergic effect for reducing nicotine. The nicotine-reducing agent also can result in a yield increase and improve the aroma of tobacco.

2 Claims, No Drawings

US 8,895,472 B2

AGENT FOR REDUCING NICOTINE AND HARMFUL COMPONENTS IN TOBACCO LEAVES FOR USE IN FIELD CULTIVATION OF TOBACCO

FIELD OF THE INVENTION

The present invention generally relates to tobacco cultivation, and more particular, to an agent for reducing nicotine and harmful components in tobacco leaves for use in field cultivation of tobacco.

BACKGROUND OF THE INVENTION

The harm of nicotine in tobacco to human health is an indisputable fact. It is well known that tobacco specific nitrosamines (TSNAs) in tobacco can result in cancers. Of them, 4-(methylnitrosamine)-1-(3-pyridine)-1-acetone (NNK) in the TSNAs is one of the most harmful components inducing cancers. The notion of which smoking is harmful to health is well-established. Therefore, in view of human health, reducing the contents of nicotine and TSNAs in tobacco as much as possible has been of interest in the tobacco industry and other industries. Presently, there exist the following approaches to reduce nicotine and/or TSNAs in tobacco.

I. Nicotine inhaled into an organism is reduced by utilizing formulation technologies in production processes of tobacco products, thereby reducing the content of nicotine and or TSNAs. For example, as disclosed in Chinese Patent Publication No. CN1351852A, additives such as tea polyphenols, potassium citrate, potassium tartrate, and tannin are added into the formulation of tobacco to reduce the content of nicotine. As disclosed in Chinese Patent Publication No. CN1757337, additives prepared with porphyrin compound are added to the filters of cigarettes and/or tobacco blend of cigarettes, so as to reduce the content of TSNAs. Further, as disclosed in Chinese Patent Publication No. CN101015391, a composite additive containing a tobacco extract, an alkali metal salt and a metal hydroxide is added to tobacco leaves or tobacco blend, so as to reduce the content of TSNAs. In this approach, certain additives are expensive. Although some additives are of natural ingredients, the extraction procedures of active ingredients are troublesome and laborious. Additionally, some additives are of inorganic chemical ingredients, which may have risks in harmful residues.

II. Harvested tobacco leaves are treated with plant-derived agents or microbial preparations to directly reduce the nicotine content in tobacco. For example, as disclosed in Chinese Patent Publication No. CN101288504A, an ixeris denticulata extract is sprayed onto sun-baked tobacco leaves, and then naturally dried in shade, so as to reduce the nicotine content in tobacco. As disclosed in Chinese Patent Publication Nos. CN1579260 and CN1580237, microbial preparations containing strains KenLxP30 and KenLXR34 are applied respectively, so as to reduce the TSNAs content in tobacco. However, such an approach definitely increases the process steps and equipment for cigarette production. In addition, improper controls may cause the impairment to sensory quality of the tobacco.

III. Another approach is to reduce of the nicotine content in tobacco leaves when tobacco is planted and cultivated in the field.

1. Tea fertilizer is applied to the soil to reduce the nicotine content in tobacco. This approach has certain effects, but is very costly. There are limitations in a large-scale field cultivation of tobacco.

2. Microorganisms or microorganism metabolites are directly used to reduce nicotine in ripe tobacco leaves, so as to directly reduce the nicotine content in tobacco. For example, as disclosed in Chinese Patent Nos. ZL200410079650.6 and ZL200410079651.0, biological preparations prepared with Arthrobacter strains AS-1 and AS-2 are respectively used to reduce the nicotine content in tobacco. Although the cost of agent production is low, there are difficulties in the temperature and humidity controls in the tobacco curing process.

3. Growth hormones or other chemical agents are applied to the plant, so as to reduce the nicotine content in tobacco. For example, in "Regulating Effect of Nicotine Content of Flue-Cured Tobacco with Exogenous Regulators" (Feng, Ding, Thesis for Degree of Master, Nanjing Agricultural University, 2006), Feng Ding proposes to use 2,4-dichlorophenoxyacetic acid (2,4-D) or a combined agent of $BF_1$ and choline chloride (CC) to reduce the nicotine content in tobacco. The nicotine reducing agent such as 2,4-D and CC has significant effects in nicotine reduction. However, applications of a chlorine element in a large amount not only are harmful to the ecological environment, but also cause chlorine remaining in tobacco, which is prohibited for tobacco.

Additionally, in "Effects of exogenous IAA on activity of ODC, MPO, MPT and nicotine content in flue-cured tobacco" (Acta Tabacaria Sinica, 2005, 11(6)), Huashan Liu et al report that certain effects are achieved by using indolylacetic acid to reduce the nicotine content. In "Effects of Nitrogen, Remained Leaves and α-NAA on the Nicotine of Flue-cured Tobacco Variety K326", (Journal of Shanxi Agricultural University 2005, 25(3)), Wenxia Gao et al report that certain effects are also achieved by using naphthylacetic acid (α-NAA). However, in both chemical adjustment methods, a single ingredient is used, and the nicotine reducing level is limited. Further, the yield is not so stable. Thus, the two methods have little value of applications. Currently, no report regarding methods of applying exogenous salicylic acid and salicylic acid in combination with naphthylacetic acid or indolylacetic acid to reduce the nicotine content in tobacco is available domestically and internationally.

With respect to applications of salicylic acid in the field of plant cultivation, salicylic acid is an exogenous regulator for improving synthesis and metabolism of a target ingredient in the field of plant cultivation. Roles of salicylic acid as signaling molecule in plant disease resistant response and as stress resistant signaling molecule for inducing a plant to respond to abiotic stresses such as drought, low temperature, and saline damage are reported in many plant physiology researches. For example, application of 2 mmol/L salicylic acid can alleviate the damage of drought stress to bean seedling, application of 0.5 mmol/L salicylic acid can enhance the tolerance of corn to low temperature, and application of 0.1 g/L salicylic acid can improve the resistance of wheat to saline damage (Xin Sun, Yunmei Guo et al., Effects of Salicylic Acid on Several Physiological Indexes of Kidney Bean under Water Stress [J]. Journal of Sichuan University, 2005, 42(3); and Yifan Zhang, Mi'na Zhu, Discussion on Physiological Effect of Salicylic Acid in Plants [J]. China New Technologies and Products, 2009(1)). In addition, Chinese Patent Publication No. CN1476756 discloses the use of salicylic acid in growth regulation, which uses a composition containing salicylic acid or a salt thereof, amino acids and vitamins to improve potassium content and disease resistance of tobacco. Furthermore, in U.S. Pat. No. 7,691,630, a preparation containing salicylic acid is applied to improve the disease resistance of plants, so as to improve the yield and quality of crops. However, so far, in the field planting and cultivation of tobacco there have been no patents or literatures regarding application of aqueous salicylic acid solution or a mixed solution of salicylic acid and naphthylacetic acid or indolylacetic acid in water to reduce nicotine and (or) TSNAs in tobacco leaves.

Therefore, a heretofore unaddressed need exists in the art to address the aforementioned deficiencies and inadequacies

SUMMARY OF THE INVENTION

Accordingly, the present invention is directed to an agent for reducing nicotine and harmful components in tobacco leaves for use in the field cultivation of tobacco. Plant regulatory chemical agents are applied to tobacco plants planted and cultivated in the field, so that nicotine and TSNAs and other harmful components are reduced, and the quality of the tobacco leaves are improved fully, thereby achieving the purpose of reducing nicotine and harmful components at the source of tobacco cultivation, and lowering the hazard caused by tobacco products to human health as much as possible. In addition, the agent for reducing nicotine and harmful components in tobacco leaves according to the present invention is an aqueous solution of a low content, and has the advantages of small dosage, low cost, convenient application, being absorbable by plants and degradable in the nature, and being harmless to human and the environment.

The present invention is implemented by adopting the following technical solutions.

On aspect of the present invention provides an agent for reducing nicotine and harmful components in tobacco leaves for use in planting and cultivation of tobacco in the field, which contains a plant regulatory chemical agent, i.e. an aqueous solution of salicylic acid (SA); or a mixed solution of salicylic acid (SA) and naphthylacetic acid (NAA) and/or indolylacetic acid (IAA) in water. The agent for reducing nicotine and harmful components is applied to the tobacco plants in a topping period in planting and cultivation of tobacco, so as to reduce nicotine and TSNAs contents in ripe tobacco leaves and fully improve the quality of the tobacco leaves. In one embodiment, the ingredients and contents thereof based on a weight percent in the formulation of the agent for reducing nicotine and harmful components in tobacco leaves are as follows:

| | |
|---|---|
| salicylic acid (SA) | 0.005%-0.16%, |
| naphthylacetic acid (NAA) | 0-0.003%, |
| indolylacetic acid (IAA) | 0-0.015%, and |
| purified water | added up to 100%. |

According to the ingredients and contents thereof based on the weight percent in the formulation of the agent for reducing nicotine and harmful components for tobacco leaves, embodiments of the present invention provides the following four formulations of the agent for reducing nicotine and harmful components in tobacco leaves having ingredients and contents thereof as follows.

I. When the content of naphthylacetic acid (NAA) in the formulation is 0, and the content of indolylacetic acid (IAA) is not 0, that is, merely naphthylacetic acid (NAA) is absent, the formulation is a mixed solution of salicylic acid (SA) and indolylacetic acid (IAA) in water:

| | |
|---|---|
| salicylic acid (SA) | 0.005%-0.16%, |
| indolylacetic acid (IAA) | >0 to 0.015%, and |
| purified water | added up to 100%. |

II. When the content of indolylacetic acid (IAA) in the formulation is 0, and the content of naphthylacetic acid (NAA) is not 0, that is, merely indolylacetic acid (IAA) is absent, the formulation is a mixed solution of salicylic acid (SA) and naphthylacetic acid (NAA) in water:

| | |
|---|---|
| salicylic acid (SA) | 0.005%-0.16%, |
| naphthylacetic acid (NAA) | >0 to 0.003%, and |
| purified water | added up to 100%. |

III. When either of the contents of naphthylacetic acid (NAA) and indolylacetic acid (IAA) content is not 0, that is, both naphthylacetic acid (NAA) and indolylacetic acid (IAA) are present, the formulation is an aqueous solution of salicylic acid (SA), naphthylacetic acid (NAA) and indolylacetic acid (IAA):

| | |
|---|---|
| salicylic acid (SA) | 0.005%-0.16%, |
| naphthylacetic acid (NAA) | >0 to 0.003% |
| indolylacetic acid (IAA) | >0 to 0.015%, and |
| purified water | added up to 100%. |

IV. When the contents of naphthylacetic acid (NAA) and indolylacetic acid (IAA) in the formulation are both 0, that is, both naphthylacetic acid (NAA) and indolylacetic acid (IAA) are absent, the formulation is a single solution of salicylic acid (SA) in water:

| | |
|---|---|
| salicylic acid (SA) | 0.005%-0.16%, and |
| purified water | added up to 100%. |

The agent for reducing nicotine and harmful components in tobacco leaves according to one embodiment of the present invention is applied in the field through the following method.

After the tobacco plants planted and cultivated in the field are topped, the aqueous solution of the agent for reducing nicotine and harmful components in tobacco leaves is formulated according to the ingredients and contents above, in which salicylic acid and naphthylacetic acid respectively are first dissolved in about 5-10 mL of 95% ethanol, and then dissolved in clean water. After formulation, the solution is applied at one time by spraying or root pouring at a dosage of about 50-300 mL per plant. When being implemented with a sleeve, absorbent cotton in the sleeve is immersed in the solution for about 2-7 days, and then applied to the plants following the existing method.

After the tobacco leaves are ripe, the contents of nicotine and TSNAs in the tobacco leaves are significantly reduced.

The present invention has technical progresses and inventive steps.

Due to the antipyretic and analgesic effects, the chemical agent salicylic acid is widely used as an external application drug in the medicine field for a long period of time, by being formulated into a salicylic acid ointment. In the recent ten years, salicylic acid is used in the filed of plant planting as an exogenous growth hormone able to improve the synthesis and metabolism of a target ingredient. However, salicylic acid is only reported in plant physiology researches as a signaling molecule in plant disease resistant response and for inducing plants to respond to abiotic stresses such as drought, low temperature, and saline damage, and the use of salicylic acid as an agent for reducing nicotine and harmful components in tobacco leaves in tobacco planting is not reported.

The contribution of the present invention lies in that the application of salicylic acid as a chemical agent belong to plant hormones having regulatory effect in tobacco field is creatively developed. The nicotine and TSNAs contents in tobacco are significantly reduced in a conventional planting mode by applying an aqueous solution of salicylic acid with a specified content in the field cultivation of tobacco, and a synergistic effect is further achieved by using in combination with a plant regulator belonging to growth hormones, that is, naphthylacetic acid (NAA) or indolylacetic acid (IAA). Therefore, the use of the agent for reducing nicotine and harmful components in tobacco leaves according to embodiments of the present invention in planting and cultivation of tobacco in the field can not only significantly reduce the contents of nicotine and TSNAs in tobacco in a conventional planting mode, but also improve the ripeness and sugar/nicotine ratio of tobacco leaves, so that the aroma quality and the aroma amount of tobacco are improved. Meanwhile, the weight per leaf of the tobacco leaves is also increased, and thus a comprehensive effect of nicotine and harmful components reduction, yield increase, and aroma improvement of tobacco is exhibited. In addition, the chemical agents involved in the present invention are a chemical agent belonging to plant hormones and a plant regulatory chemical agent belonging to growth hormones. The chemical agents do not cause pollution, are harmless, can be naturally degraded and used at a low dosage, have a low cost, and are very convenient for field application.

The agent for reducing nicotine and harmful components in tobacco leaves according to embodiments of the present invention has significant effect in reducing nicotine and harmful components. When applied to Burley tobacco, the agent can reduce nicotine in tobacco leaves by about 13.6%-51.8%, and reduce TSNAs by 32.6%-41.0%, in which NNK in TSNAs is reduced by 28.6%-37.3%; and when applied to flue-cured tobacco, the agent can reduce nicotine in tobacco leaves by 1.1%-22.3%, and reduce TSNAs by 28.6%-35.7%, in which NNK in TSNAs is reduced by 33.8%-42.3%.

These and other aspects of the present invention will become apparent from the following description of the preferred embodiments, although variations and modifications therein may be affected without departing from the spirit and scope of the novel concepts of the disclosure.

DETAILED DESCRIPTION OF THE INVENTION

Without intent to limit the scope of the invention, additional exemplary embodiment and their related results according to the embodiments of the present invention are given below.

EXAMPLE 1

In a Burley tobacco field in a conventional planting mode, after the tobacco plants were topped, a mixed solution of 0.040% (the weight percent, the same as below) salicylic acid and 0.001% naphthylacetic acid in water was sprayed at a dosage of 100 mL/plant on leaves at one time at the same day. The tobacco plants were ripe and harvested in the field, and samples were taken for analysis. As a result, nicotine in Burley tobacco was reduced by 13.6%-51.8%, TSNAs were reduced by 32.6%-41.0%, in which NNK in TSNAs was reduced by 28.6%-37.3%, the dry weight gain per leaf was 6.5%-12.6%, the aroma quality was increased from 12.4 to 14.1, and the aroma amount is increased from 13.5 to 16.2.

EXAMPLE 2

In a flue-cured tobacco field in a conventional planting mode, after the tobacco plants were topped, a mixed solution of 0.005% salicylic acid and 0.004% indolylacetic acid in water was sprayed at a dosage of 80 mL/plant on leaves at one time at the same day. The tobacco plants were ripe and harvested in the field, and samples were taken for analysis. As a result, nicotine was reduced by 1.1%-20.2%, TSNAs were reduced by 28.6%-35.7%, in which NNK in TSNAs was reduced by 33.8%-42.3%, the dry weight gain per leaf was 4.5%-11.8%, the aroma quality was increased from 14.0 to 15.4, the aroma amount was increased from 13.9 to 14.2, the sensory quality of the middle portion of the leaves was kept at a "good" level, and the total score of the sensory quality of the upper portion of the tobacco leaves was improved from a "moderate+" level to a "good" level.

EXAMPLE 3

In a Burley tobacco field in a conventional planting mode, a sleeve wrapped with absorbent cotton absorbing a mixed solution of 0.080% salicylic acid and 0.005% naphthylacetic acid in water was sleeved at the top of the tobacco plant, one sleeve per plant, immediately after the tobacco plants were topped. The tobacco plants were ripe and harvested in the field, and samples were taken for analysis. As a result, nicotine in Burley tobacco was reduced by 23.5%-48.6%, TSNAs were reduced by 29.8%-40.7%, with NNK in TSNAs being reduced by 29.6%-31.9%, the dry weight gain per leaf was 5.5%-11.8%, the aroma quality was increased from 13.5 to 15.8, and the aroma amount was increased from 13.8 to 15.1.

EXAMPLE 4

In a Burley tobacco field in a conventional planting mode, after the tobacco plants were topped, 0.100% solution of salicylic acid in water was sprayed at a dosage of 120 mL/plant on the leaves at one time at the same day. The tobacco plants were ripe and harvested in the field, and samples were taken for analysis. As a result, nicotine in Burley tobacco was reduced by 14.4%-40.4%, TSNAs were reduced by 33.5%-38.2%, with NNK in TSNAs being reduced by 28.9%-30.3%, the dry weight gain per leaf was 4.7%-10.3%, the aroma quality was increased from 13.2 to 15.9, and the aroma amount was increased from 14.3 to 16.7.

EXAMPLE 5

In a flue-cured tobacco field in a conventional planting mode, after the tobacco plants were topped, a mixed solution of 0.035% salicylic acid, 0.002% indolylacetic acid and 0.001% naphthylacetic acid in water was sprayed at a dosage of 50 mL/plant on leaves at one time at the same day. The tobacco plants were ripe and harvested in the field, and samples were taken for analysis. As a result, nicotine in the flue-cured tobacco was reduced by 6.1%-22.3%, TSNAs were reduced by 29.1%-34.7%, with NNK in TSNAs being reduced by 34.9%-42.1%, the dry weight gain per leaf was 5.8%-14.8%, the aroma quality was increased from 13.8 to 15.7, the aroma amount was increased from 13.6 to 14.6, the sensory quality of the middle portion of the leaves was stably kept at a "good" level, and the total score of the sensory quality of the upper portion of the tobacco leaves was improved from a "moderate+" level to a "good" level.

EXAMPLE 6

In a Burley tobacco field in a conventional planting mode, after the tobacco plants were topped, a mixed solution containing 0.160% salicylic acid and 0.010% naphthylacetic acid in water was poured towards roots at the same day, 300 mL solution per plant to the soil nearby the root. The tobacco plants were ripe and harvested in the field, and samples were taken for analysis. As a result, nicotine in Burley tobacco was reduced by 16.9%-35.2%, TSNAs were reduced by 32.7%-39.1%, with NNK in TSNAs being reduced by 28.7%-33.3%, the dry weight gain per leaf was 4.9%-10.8%, the aroma quality was increased from 14.2 to 16.5, and the aroma amount was increased from 14.4 to 16.3.

Note that the aroma quality and the aroma amount are dimensionless, and the sensory appraisal scores thereof are evaluated according to Tobacco Industry Standard YC/T138 "Tobacco and tobacco products—The sensory evaluation methods".

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference were individually incorporated by reference.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A method for field application of an agent for reducing nicotine and harmful components in tobacco leaves for use in the field cultivation of tobacco, comprising: after tobacco plants planted and cultivated in the field are topped, formulating the agent, applying by using a sleeve wrapped with absorbent cotton impregnated with the agent and sleeved at the top of topped tobacco plants, wherein the agent consists of:

| | |
|---|---|
| salicylic acid (SA) | 0.08%; |
| naphthylacetic acid (NAA) | 0.005%; and |
| purified water | added up to 100%; and | wherein the reducing nicotine and harmful components in tobacco leaves comprises reducing tobacco specific nitrosamines (TSNAs).

2. A method for field application of an agent for reducing nicotine and harmful components in tobacco leaves for use in the field cultivation of tobacco, comprising: after tobacco plants planted and cultivated in the field are topped, formulating the agent, and applying the agent by spraying to the topped tobacco plants, wherein the agent consists of:

| | |
|---|---|
| salicylic acid (SA) | 0.035%; |
| naphthylacetic acid (NAA) | 0.002%; |
| indolylacetic acid (IAA) | 0.001%; and |
| purified water | added up to 100%; and | wherein the reducing nicotine and harmful components in tobacco leaves comprises reducing tobacco specific nitrosamines (TSNAs).

* * * * *